(12) United States Patent
Hughes et al.

(10) Patent No.: US 6,720,407 B1
(45) Date of Patent: Apr. 13, 2004

(54) METHOD FOR ADMINISTERING INSULINOTROPIC PEPTIDES

(75) Inventors: Benjamin Lee Hughes, Indianapolis, IN (US); Ronald Keith Wolff, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/383,789

(22) Filed: Aug. 26, 1999

Related U.S. Application Data

(60) Provisional application No. 60/100,012, filed on Sep. 11, 1998, and provisional application No. 60/098,273, filed on Aug. 28, 1998.

(51) Int. Cl.$^7$ ............................................... A61K 38/16
(52) U.S. Cl. ..................... 530/324; 514/12; 424/489; 424/499; 530/308
(58) Field of Search ................................ 530/308, 324; 514/12; 424/489, 499

(56) References Cited

U.S. PATENT DOCUMENTS

| | | | | |
|---|---|---|---|---|
| 5,118,666 A | * | 6/1992 | Habener | 514/12 |
| 5,120,712 A | * | 6/1992 | Habener | 514/12 |
| 5,512,549 A | * | 4/1996 | Chen | 514/12 |
| 5,545,618 A | * | 8/1996 | Buckley | 514/2 |
| 5,574,008 A | * | 11/1996 | Johnson | 514/12 |
| 5,705,483 A | * | 1/1998 | Galloway | 514/12 |
| 5,846,937 A | * | 12/1998 | Drucker | 514/12 |
| 5,908,830 A | * | 6/1999 | Smith | 514/12 |
| 5,977,071 A | | 11/1999 | Galloway et al. | 514/12 |

FOREIGN PATENT DOCUMENTS

| | | |
|---|---|---|
| WO | WO 93/18785 A | 9/1993 |
| WO | 0 619 322 A | 10/1994 |
| WO | WO 98/08871 A | 3/1998 |
| WO | WO 98/19698 A | 5/1998 |
| WO | 98/20895 * | 5/1998 |
| WO | WO 99/03454 A | 1/1999 |

OTHER PUBLICATIONS

Patton, J.S., et al., "Pulmonary Absorption and Metabolism of Peptides and Proteins," 1998, *Respiratory Drug Delivery* VI:17–24.

Deacon, D.F., et al., "Dipeptidyl peptidase IV resistant analogues of glucagon–like peptide–1 which have extended metabolic stability and improved biological activity," 1998, *Diabetologia* 41:271–278.

Ritzel, U., et al., "A synthetic glucagon–like peptide–1 analog with improved plasma stability," 1998, *Journal of Endocrinology* 159:93–102.

Wearley, L.L., "Recent progress in protein and peptide delivery by noninvasive routes." 1991, *Crit. Rev. Ther. Drug Carrier Sys.* 8:331–394.

Byron, P.R. and J.S. Patton, "Drug Delivery via the Respiratory Tract." 1994, *J. Aerosol Med.* 7:49–75.

Niven, R. W., "Delivery of biotherapeutics by inhalation aerosol." 1995, *Crit. Rev. Ther. Drug Carrier Syst.* 12:151–231.

Laube, B.L., et al., "Preliminary study of the efficacy of insulin aerosol delivered by oral inhalation in diabetic patients." 1993, *JAMA* 269:2106–2109.

Kobayashi, S., et al., "Critical factors on pulmonary absorption of peptides and proteins (diffusional barrier and metabolic barrier)." 1996, *Eur. J. Pharm. Sci.* 4:367–372.

Adjei, A.L. and P.J. Carrigan, "Pulmonary bio–availability of LH–RH analogs: Some bio–pharmaceutical guidelines." 1992, *J. Biopharm. Sci.* 3:247–254.

Patton, J. S. and R.M. Platz, "Pulmonary delivery of peptides and proteins for systemic action." 1992, *Adv. Drug Deliv. Rev.* 8:179–196.

* cited by examiner

*Primary Examiner*—Christopher S. F. Low
*Assistant Examiner*—David Lukton
(74) *Attorney, Agent, or Firm*—Gregory A. Cox

(57) ABSTRACT

The claimed invention relates to a method of administering glucagon-like peptide-1 molecules by inhalation, a method for treating diabetes by administering glucagon-like peptide-1 molecules by inhalation, and a method for treating hyperglycemia by administering glucagon-like peptide-1 molecules by inhalation.

28 Claims, No Drawings

SEQUENCE LISTING

<160> NUMBER OF SEQ ID NOS: 4

<210> SEQ ID NO 1
<211> LENGTH: 29
<212> TYPE: PRT
<213> ORGANISM: Artificial Sequence
<220> FEATURE:
<223> OTHER INFORMATION: synthetic construct
<221> NAME/KEY: PEPTIDE
<222> LOCATION: (1)..(1)
<223> OTHER INFORMATION: X at position 1 is Ala, Gly, Val, Thr, Ile and
     alpha-methyl-Ala;
<221> NAME/KEY: PEPTIDE
<222> LOCATION: (14)..(14)
<223> OTHER INFORMATION: X at position 14 is Glu, Gln, Ala, Thr, Ser and
     Gly;
<221> NAME/KEY: PEPTIDE
<222> LOCATION: (20)..(20)
<223> OTHER INFORMATION: X at position 20 is Glu, Gln, Ala, Thr, Ser and
     Gly.

<400> SEQUENCE: 1

```
Xaa Glu Gly Thr Phe Thr Ser Asp Val Ser Ser Tyr Leu Xaa Gly Gln
1               5                   10                  15

Ala Ala Lys Xaa Phe Ile Ala Trp Leu Val Lys Gly Arg
            20                  25

<210> SEQ ID NO 2
<211> LENGTH: 29
<212> TYPE: PRT
<213> ORGANISM: Artificial Sequence
<220> FEATURE:
<223> OTHER INFORMATION: synthetic construct
<221> NAME/KEY: PEPTIDE
<222> LOCATION: (28)..(28)
<223> OTHER INFORMATION: X at position 28 is Lys;
<221> NAME/KEY: PEPTIDE
<222> LOCATION: (29)..(29)
<223> OTHER INFORMATION: X at position 29 is Gly or is absent.

<400> SEQUENCE: 2

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Xaa Xaa
            20                  25

<210> SEQ ID NO 3
<211> LENGTH: 29
<212> TYPE: PRT
<213> ORGANISM: Artificial Sequence
<220> FEATURE:
<223> OTHER INFORMATION: synthetic construct
<221> NAME/KEY: PEPTIDE
<222> LOCATION: (19)..(19)
<223> OTHER INFORMATION: X at position 19 is Lys or Arg.

<400> SEQUENCE: 3

Ala Glu Gly Thr Phe Thr Ser Asp Val Ser Ser Tyr Leu Glu Gly Gln
1               5                   10                  15

Ala Ala Xaa Glu Phe Ile Ala Trp Leu Val Lys Gly Arg
            20                  25

<210> SEQ ID NO 4
<211> LENGTH: 31
<212> TYPE: PRT
<213> ORGANISM: Artificial Sequence
<220> FEATURE:
<223> OTHER INFORMATION: synthetic construct

<400> SEQUENCE: 4

His Val Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30
```

METHOD FOR ADMINISTERING INSULINOTROPIC PEPTIDES

CROSS-REFERENCE

This application claims the benefit of U.S. Provisional Application No. 60/098273, filed Aug. 28, 1998, and U.S. Provisional Application No. 60/100012, filed Sep. 11, 1998.

FIELD OF THE INVENTION

This invention relates to methods of treating humans suffering from diabetes and insulin resistance. In particular, the invention relates to the pulmonary delivery of glucagon-like peptide-1 (GLP-1) and analogs thereof for systemic absorption through the lungs to eliminate the need for administering anti-diabetic compounds by injection.

BACKGROUND OF THE INVENTION

Glucagon-like peptide-1 was first identified in 1987 as a incretin hormone, a peptide secreted by the gut upon ingestion of food. Glucagon-like peptide-1 is secreted by the L-cells of the intestine after being proteolytically processed from the 160 amino acid precursor protein, preproglucagon. Cleavage of preproglucagon first yields glucagon-like peptide-1, a 37 amino acid peptide that is poorly active. A subsequent cleavage of the peptide bond between residues 6 and 7 yields biologically active glucagon-like peptide-1 referred to as GLP-1(7–37). It should be noted that this specification uses the nomenclature scheme that has developed around this hormone. By convention in the art, the amino terminus of GLP-1(7-37) has been assigned number 7 and the carboxy terminus number 37. Approximately 80% of the GLP-1(7-37) that is synthesized is amidated at the C-terminal after removal of the terminal glycine residue in the L-cells. The biological effects and metabolic turnover of the free acid GLP-1(7-37), and the amide, GLP-1(7-36)NH$^2$, are indistinguishable. As used herein, these two naturally-occurring forms will be referred to collectively as GLP-1.

GLP-1 is known to stimulate insulin secretion (insulinotropic action) causing glucose uptake by cells which decreases serum glucose levels (see, e g., Mojsov, S., *Int. J. Peptide Protein Research*, 40:333–343 (1992)). Numerous GLP-1 analogs and derivatives demonstrating insulinotropic action are known in the art. Also it has been demonstrated that the N-terminal histidine residue (His 7) is very important to insulinotropic activity of GLP-1 (Suzuki, S., et al. *Diabetes Res.; Clinical Practice* 5 (Supp. 1):S30 (1988).

Multiple authors have demonstrated the nexus between laboratory experimentation and mammalian, particularly human, insulinotropic responses to exogenous administration of GLP-1. See, e.g., Nauck, M. A., et al., *Diabetologia*, 36:741–744 (1993); Gutniak, M., et al., *New England J. of Medicine*, 326(20):1316–1322 (1992); Nauck, M. A., et al., *J. Clin. Invest.*, 91:301–307 (1993); and Thorens, B., et al., *Diabetes*, 42:1219–1225 (1993)].

GLP-1 based peptides hold great promise as alternatives to insulin therapy for patients with diabetes who have failed on sulfonylureas. GLP-1 has been studied intensively by academic investigators, and this research has established the following for patients with type II diabetes who have failed on sulfonylureas:

1) GLP-1 stimulates insulin secretion, but only during periods of hyperglycemia. The safety of GLP-1 compared to insulin is enhanced by this property of GLP-1 and by the observation that the amount of insulin secreted is proportional to the magnitude of the hyperglycemia. In addition, GLP-1 therapy will result in pancreatic release of insulin and first-pass insulin action at the liver. This results in lower circulating levels of insulin in the periphery compared to subcutaneous insulin injections.

2) GLP-1 suppresses glucagon secretion, and this, in addition to the delivery of insulin via the portal vein helps suppress the excessive hepatic glucose output in diabetic patients.

3) GLP-1 slows gastric emptying which is desirable in that it spreads nutrient absorption over a longer time period, decreasing the postprandial glucose peak.

4) Several reports have suggested that GLP-1 may enhance insulin sensitivity in peripheral tissues such as muscle and fat.

5) Finally, GLP-1 has been shown to be a potential regulator of appetite.

Meal-time use of GLP-1 based peptides offers several advantages over insulin therapy. Insulin therapy requires blood glucose monitoring, which is both expensive and painful. The glucose-dependency of GLP-1 provides an enhanced therapeutic window in comparison to insulin, and should minimize the need to monitor blood glucose. Weight gain also can be a problem with intensive insulin therapy, particularly in the obese type II diabetic patients.

The therapeutic potential for native GLP-1 is further increased if one considers its use in patients with type I diabetes. A number of studies have demonstrated the effectiveness of native GLP-1 in the treatment of insulin dependent diabetes mellitus. Similar to patients with type II diabetes, GLP-1 is effective in reducing fasting hyperglycemia through its glucagonostatic properties. Additional studies have indicated that GLP-1 also reduces postprandial glycemic excursions in type I patients, most likely through a delay in gastric emptying. These observations indicate that GLP-1 may be useful as a treatment in type I and type II patients.

To date administration of clinically proven peptide hormones and as well as GLP-1 has generally been accomplished by subcutaneous injection which is both inconvenient and unattractive. Therefore, many investigators have studied alternate routes for administering peptide hormones such as oral, rectal, transdermal, and nasal routes. Thus far, however, these routes of administration have not resulted in clinically proven peptide hormone therapy.

It has been known for a number of years that some proteins can be absorbed from the lung. For example, insulin administered by inhalation aerosol to the lung was first reported by Gaensslen in 1925. Despite the fact that a number of human and animal studies have shown that some insulin formulations can be absorbed through the lungs, pulmonary delivery of peptide hormones has not been vigorously pursued because of very low bioavailability. Larger proteins, such as cytokines and growth factors which are generally larger than 150 amino acid residues, are often readily absorbed by the cells lining the alveolar regions of the lung. Pulmonary absorption of smaller proteins is however much less predictable; though insulin (51 residues), calcitonin (32 residues) and parathyroid hormone (34 residues) have been reported to be systemically absorbed through the pulmonary route. See U.S. Pat. No: 5,607,915, herein incorporated by reference. Despite systemic absorption by the lung of some small protein hormones, the pharmacodynamics associated with pulmonary delivery of peptides is unpredictable.

Thus, there is a need to provide a reliable pulmonary method of delivering GLP-1 and related analogs because it would offer patients an attractive, non-invasive alternative to insulin. This need is particularly true since insulin has a very narrow therapeutic index while GLP-1 treatment offers a way to normalize blood glucose only in response to hyperglycemic conditions without the threat of hypoglycemia.

Not all protein hormones can be efficiently absorbed through the lungs, and there are many factors that affect it. Absorption of proteins in the lung is largely dependent on the physical characteristics of the protein. Thus, even though pulmonary delivery of some protein hormones has been observed, the physical properties and short length of GLP-1 and some related peptides made it unclear whether such peptides could be effectively delivered through the pulmonary route.

Efficient pulmonary delivery is dependent on the ability to deliver the protein to the deep lung alveolar epithelium. Protein particles that lodge in the upper airway epithelium are not absorbed to a significant extent because the overlying mucus functions to trap, and then clear debris by mucociliary transport up the airway. This mechanism is also a major contributor to low bioavailability. The extent to which proteins are not absorbed and instead eliminated by these routes depends on their solubility, their size, and other largely uncharacterized mechanisms.

Even when a peptide hormone can be reproducibly delivered to the deep lung alveolar epithelium, it is difficult to predict whether it will be rapidly absorbed and transported to the blood. Absorption values for some proteins delivered through the lungs have been calculated and range from fifteen minutes for parathyroid hormone (1-34) to 48 hours for glycosylated α1-antitrypsin. Moreover a variety of endogenous peptidases exist in the lung which can degrade peptides prior to absorption. Thus, the longer it takes for a peptide particle to dissolve and be absorbed, the greater the chance for enzymatic inactivation. Thus, because of the small size of GLP-1 and its inherent susceptibility to certain enzymes, it was most surprising to find that an aerosolized GLP-1 analog could be reproducibly and effectively delivered through the lungs.

SUMMARY OF THE INVENTION

The present invention relates to a method for administering a glucagon-like peptide-1 molecule comprising, administering an effective amount of the peptide to a patient in need thereof by pulmonary delivery. The present invention also relates to a method for treating diabetes comprising, administering an effective dose of a glucagon-like peptide-1 to a patient in need thereof by pulmonary delivery. Another aspect of the invention relates to a method for treating hyperglycemia comprising, administering an effective dose of a glucagon-like peptide-1 to a patient in need thereof by pulmonary delivery. Preferably, the glucagon-like peptide-1 molecule is delivered by inhalation and to the lower airway of the patient.

The glucagon-like peptide-1 can be delivered in a carrier, as a solution or suspension, or as a dry powder, using any of a variety of devices suitable for administration by inhalation. Preferably, the glucagon-like peptide-1 is delivered in a particle size effective for reaching the lower airways of the lung.

DETAILED DESCRIPTION OF THE INVENTION

The term "GLP-1" refers to human glucagon-like peptide-1 whose sequences and structures are known in the art. See U.S. Pat. No. 5,120,712, herein incorporated by reference. As previously discussed, there are two native forms of human GLP-1, GLP-1(7-37) and GLP-1(7-36)$NH_2$ which will be distinguished only when necessary.

The term "GLP-1 analog" is defined as a molecule having one or more amino acid substitutions, deletions, inversions, or additions compared with GLP-1. Many GLP-1 analogs are known in the art and include, for example, GLP-1(7-34) and GLP-1(7-35), GLP-1(7-36), $Val^8$-GLP-1(7-37), $Gln^9$-GLP-1(7-37), D-$Gln^9$-GLP-1(7-37), $Thr^{16}$-$Lys^{18}$-GLP-1(7-37), and $Lys^{18}$-GLP-1(7-37). Preferred GLP-1 analogs are GLP-1(7-34) and GLP-1(7-35), which are disclosed in U.S. Pat. No. 5,118,666, herein incorporated by reference.

The term "GLP-1 derivative" is defined as a molecule having the amino acid sequence of GLP-1 or a GLP-1 analog, but additionally, having chemical modification of one or more of its amino acid side groups, a-carbon atoms, terminal amino group, or terminal carboxylic acid group. A chemical modification includes, but is not limited to, adding chemical moieties, creating new bonds, and removing chemical moieties. Modifications at amino acid side groups include, without limitation, acylation of lysine e-amino groups, N-alkylation of arginine, histidine, or lysine, alkylation of glutamic or aspartic carboxylic acid groups, and deamidation of glutamine or asparagine. Modifications of the terminal amino include, without limitation, the des-amino, N-lower alkyl, N-di-lower alkyl, and N-acyl modifications. Modifications of the terminal carboxy group include, without limitation, the amide, lower alkyl amide, dialkyl amide, and lower alkyl ester modifications. Lower alkyl is $C_1$–$C_4$ alkyl. Furthermore, one or more side groups, or terminal groups, may be protected by protective groups known to the ordinarily-skilled protein chemist. The a-carbon of an amino acid may be mono- or di-methylated.

The term "GLP-1 molecules" means GLP-1, GLP-1 analog, or GLP-1 derivative.

Another preferred group of GLP-1 analogs is defined by the formula:

$R_1$-X-Glu-Gly-Thr-Phe-Thr-Ser-Asp-Val-Ser-Ser-Tyr-Leu-Gly-Gln-Ala-Ala-Lys-Z-Phe-Ile-Ala-Trp-Leu-Val-Lys-Gl y-Arg-$R_2$ (SEQ ID NO:1)

and the pharmaceutically-acceptable salts thereof, wherein: $R_1$ is selected from the group consisting of L-histidine, D-histidine, desamino-histidine, 2-amino-histidine, b-hydroxy-histidine, homohistidine, alpha-fluoromethyl-histidine, and alpha-methyl-histidine; X is selected from the group consisting of Ala, Gly, Val, Thr, Ile, and alpha-methyl-Ala; Y is selected from the group consisting of Glu, Gln, Ala, Thr, Ser, and Gly; Z is selected from the group consisting of Glu, Gln, Ala, Thr, Ser, and Gly; and $R_2$ is selected from the group consisting of $NH_2$, and Gly-OH; providing that when $R_1$ is His, X is Ala, Y is Glu, and Z is Glu, $R_2$ must be $NH_2$.

Yet another preferred group of compounds consistent with the present invention is disclosed in WO 91/11457 (U.S. Pat. No. 5,545,618, herein incorporated by reference) and consists essentially of GLP-1(7-34), GLP-1(7-35), GLP-1(7-36), or GLP-1(7-37), or the amide forms thereof, and pharmaceutically-acceptable salts thereof, having at least one modification selected from the group consisting of:

(a) substitution of glycine, serine, cysteine, threonine, asparagine, glutamine, tyrosine, alanine, valine, isoleucine, leucine, methionine, phenylalanine, arginine, or D-lysine for lysine at position 26 and/or position 34; or substitution of glycine, serine, cysteine, threonine, asparagine, glutamine, tyrosine, alanine, valine, isoleucine, leucine, methionine, phenylalanine, lysine, or a D-arginine for arginine at position 36;

(b) substitution of an oxidation-resistant amino acid for tryptophan at position 31;

(c) substitution of at least one of: tyrosine for valine at position 16; lysine for serine at position 18; aspartic acid for glutamic acid at position 21; serine for glycine at position 22; arginine for glutamine at position 23; arginine for alanine at position 24; and glutamine for lysine at position 26; and (d) substitution of at least one of: glycine, serine, or cysteine for alanine at position 8; aspartic acid, glycine, serine, cysteine, threonine, asparagine, glutamine, tyrosine, alanine, valine, isoleucine, leucine, methionine, or phenylalanine for glutamic acid at position 9; serine, cysteine, threonine, asparagine, glutamine, tyrosine, alanine, valine, isoleucine, leucine, methionine, or phenylalanine for glycine at position 10; and glutamic acid for aspartic acid at position 15; and (e) substitution of glycine, serine, cysteine, threonine, asparagine, glutamine, tyrosine, alanine, valine, isoleucine, leucine, methionine, or phenylalanine, or the D- or N-acylated or alkylated form of histidine for histidine at position 7; wherein, in the substitutions is (a), (b), (d), and (e), the substituted amino acids can optionally be in the D-form and the amino acids substituted at position 7 can optionally be in the N-acylated or N-alkylated form.

Because the enzyme, dipeptidyl-peptidase IV (DPP IV), may be responsible for the observed rapid in vivo inactivation of administered GLP-1, [see, e.g., Mentlein, R., et al., *Eur. J. Biochem.*, 214:829–835 (1993)], administration of GLP-1 analogs and derivatives that are protected from the activity of DPP IV is preferred, and the administration of Gly$^8$-GLP-1(7-36)NH$_2$, Val$^8$-GLP-1(7-37)OH, a-methyl-Ala$^8$-GLP-1(7-36)NH$_2$, and Gly$^8$-Gln $^{21}$-GLP-1(7-37)OH, or pharmaceutically-acceptable salts thereof, is more preferred.

The use in the present invention of a molecule claimed in U.S. Pat. No. 5,188,666, herein incorporated by reference, is preferred. Such molecule is selected from the group consisting of a peptide having the amino acid sequence:

His-Ala-Glu-Gly-Thr-Phe-Thr-Ser-Asp-Val-Ser-Ser-Tyr-Leu-Glu-
Gly-Gln-Ala-Ala-Lys-Glu-Phe-Ile-Ala-Trp-Leu-
Val-X    (SEQ ID NO:2)

wherein X is selected from the group consisting of Lys and Lys-Gly; and a derivative of said peptide, wherein said peptide is selected from the group consisting of: a pharmaceutically-acceptable acid addition salt of said peptide; a pharmaceutically-acceptable carboxylate salt of said peptide; a pharmaceutically-acceptable lower alkylester of said peptide; and a pharmaceutically-acceptable amide of said peptide selected from the group consisting of amide, lower alkyl amide, and lower dialkyl amide.

Another preferred group of molecules for use in the present invention consists of compounds disclosed in U.S. Pat. No. 5,512,549, herein incorporated by reference, having the general formula:

(SEQ ID NO:3)

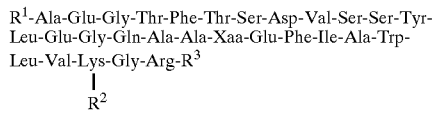

and pharmaceutically-acceptable salts thereof, wherein R$^1$ is selected from the group consisting of 4-imidazopropionyl, 4-imidazoacetyl, or 4-imidazo-a, a dimethyl-acetyl; R$^2$ is selected from the group consisting of C$_6$–C$_{10}$ unbranched acyl, or is absent; R$^3$ is selected from the group consisting of Gly-OH or NH$_2$; and, Xaa is Lys or Arg, may be used in present invention.

More preferred compounds of SEQ ID NO:3 for use in the present invention are those in which Xaa is Arg and R$^2$ is C$_6$–C$_{10}$ unbranched acyl.

Highly preferred compounds of SEQ ID NO:3 for use in the present invention are those in which Xaa is Arg, R$^2$ is C$_6$–C$_{10}$ unbranched acyl, and R$_2$ is Gly-OH.

More highly preferred compounds of SEQ ID NO:3 for use in the present invention are those in which Xaa is Arg, R$^2$ is C$_6$–C$^{10}$ unbranched acyl, R$^3$ is Gly-OH, and R is 4-imidazopropionyl.

The most preferred compound of SEQ ID NO:3 for use in the present invention is that in which Xaa is Arg, R$^2$ is C$_8$ unbranched acyl, R$^3$ is Gly-OH, and R$^1$ is 4-imidazopropionyl.

The use of Val$^8$ -GLP-1(7-37)OH or a pharmaceutically-acceptable salt thereof, as claimed in U.S. Pat. No. 5,705,483, herein incorporated by reference, in the present invention is highly preferred.

Methods for preparing the GLP-1, GLP-1 analogs, or GLP-1 derivatives useful in the present invention are well-known in the art and are easily within the grasp of ordinarily skilled protein chemists or biochemists. The amino acid portion of the active compound used in the present invention, or a precursor thereto, can be made either by solid-phase synthetic chemistry, purification of GLP-1 molecules from natural sources, or recombinant DNA technology. Routine synthetic organic techniques enable the alkylation and acylation of the GLP-1 derivatives.

The term "GLP-1 related compound" refers to any compound falling within the GLP-1, GLP-1 analog, or GLP-1 derivative definition.

The term "preservative" refers to a compound added to a pharmaceutical formulation to act as an anti-microbial agent. A parenteral formulation must meet guidelines for preservative effectiveness to be a commercially viable multi-use product. Among preservatives known in the art as being effective and acceptable in parenteral formulations are benzalkonium chloride, benzethonium, chlorohexidine, phenol, m-cresol, benzyl alcohol, methylparaben, chlorobutanol, o-cresol, p-cresol, chlorocresol, phenylmercuric nitrate, thimerosal, benzoic acid, and various mixtures thereof. See, e.g., Wallhauser, K., *Develop. Biol. Standard*, 24: 9–28 (Basel, S. Krager, 1974).

The term "buffer" or "pharmaceutically acceptable buffer" refers to a compound that is known to be safe for use in protein formulations and that has the effect of controlling the pH of the formulation at the pH desired for the formulation. Pharmaceutically acceptable buffers for controlling pH at a moderately acid pH to moderately basic pH include, for example, such compounds as phosphate, acetate, citrate, TRIS, arginine, or histidine.

The term "isotonicity agent" refers to a compound that is tolerated physiologically and imparts a suitable tonicity to a formulation to prevent the net flow of water across the cell membrane. Compounds, such as glycerin, are commonly used for such purposes at known concentrations. Other acceptable isonicity agents include salts and sugars, e.g., NaCl, dextrose, mannitol, and lactose. Glyerol at a concentration of 12 to 25 mg/mL is preferred as an isotonicity agent.

GLP-1 related compounds described above are administered by inhalation in a dose effective manner to introduce circulating therapeutic level which results in reducing abnormally high blood glucose levels. Therapeutic serum levels of GLP-1 are in the range of 0.1 to about 10.0 ng/ml, preferably about 0.3 to about 5.0 ng/ml and most preferably about 0.5 to about 3.0 ng/ml. Such administration can be effective for treating disorders such as diabetes, hyperglycemia, or insulin resistance. Achieving therapeutically effective doses of GLP-1 related compounds requires administering an inhalation dose of about 0.5 µg/kg to about 100 µg/kg of the GLP-1molecule preferably about 1.0 µg/kg to about 50 µg/kg, more preferably about 2.0 µg/kg to about 25 µg/kg, and most preferably about 2.5 µg/kg to about 15 µg/kg. A therapeutically effective amount can be determined by a knowledgeable practitioner, who will take into account factors including native GLP-1 blood levels, blood glucose levels, the physical condition of the patient, the patient's pulmonary status, and the like.

According to the invention, GLP-1 and GLP-1 analogs and derivatives are delivered by inhalation to achieve rapid absorption in the lungs. Administration by inhalation can result in pharmacokinetics comparable to subcutaneous administration of these substances. Inhalation of GLP-1 and GLP-1 analogs and derivatives leads to a rise in the level of circulating insulin followed by a rapid fall in blood glucose levels. Different inhalation devices typically provide similar pharmacokinetics when similar particle sizes and similar levels of lung deposition are compared.

According to the invention, GLP-1 and GLP-1 analogs and derivatives can be delivered by any of a variety of inhalation devices known in the art for administration of a therapeutic agent by inhalation. These devices include metered dose inhalers, nebulizers, dry powder inhalers, sprayers, and the like. Preferably, GLP-1 and GLP-1 analogs and derivatives are delivered by a dry powder inhaler or a sprayer. There are a several desirable features of an inhalation device for administering GLP-1 and GLP-1 analogs and derivatives. For example, delivery by the inhalation device is advantageously reliable, reproducible, and accurate. The inhalation device should deliver small particles, e.g. less than about 10 µm mass median aerodynamic diameter (MMAD), preferably about 1–5 µm MMAD, for good respirability. Some specific examples of commercially available inhalation devices, or those in late stage development, suitable for the practice of this invention are Turbohaler™ (Astra), Rotahaler® (Glaxo) Diskus® (Glaxo), Spiros™ inhaler (Dura), devices being developed by Inhale Therapeutics, AERx™ (Aradigm), the Ultravent® nebulizer (Mallinckrodt), the Acorn II® nebulizer (Marquest Medical Products), the Ventoline® metered dose inhaler (Glaxo), the Spinhaler® powder inhaler (Fisons), or the like.

As those skilled in the art will recognize, the formulation of GLP-1 and GLP-1 analogs and derivatives, the quantity of the formulation delivered, and the duration of administration of a single dose depend on the type of inhalation device employed. For some aerosol delivery systems, such as nebulizers, the frequency of administration and length of time for which the system is activated will depend mainly on the concentration of the GLP-1 molecule in the aerosol. For example, shorter periods of administration can be used at higher concentrations of GLP-1 and GLP-1 analogs and derivatives in the nebulizer solution. Devices such as metered dose inhalers can produce higher aerosol concentrations, and can be operated for shorter periods to deliver the desired amount of GLP-1 and GLP-1 analogs and derivatives. Devices such as powder inhalers deliver active agent until a given charge of agent is expelled from the device. In this type of inhaler, the amount of GLP-1 and GLP-1 analogs and derivatives in a given quantity of the powder determines the dose delivered in a single administration.

The particle size of the GLP-1 and GLP-1 analogs and derivatives in the formulation delivered by the inhalation device is critical with respect to the ability of protein to deposit in the lungs, and preferably in the lower airways or alveoli. Preferably, the GLP-1 and GLP-1 analogs and derivatives is formulated so that at least about 10% of the peptide delivered is deposited in the lung, preferably about 10% to about 20%, or more. It is known that the maximum efficiency of pulmonary deposition for mouth breathing humans is obtained with particle sizes of about 2 µm to about 3 µm MMAD. When particle sizes are above about 5 µm MMAD, pulmonary deposition decreases substantially. Particle sizes below about 1 µm MMAD cause pulmonary deposition to decrease, and it becomes difficult to deliver particles with sufficient mass to be therapeutically effective. Thus, particles of GLP-1 and GLP-1 analogs and derivatives delivered by inhalation have a particle size preferably less than about 10 µm MMAD, more preferably in the range of about 1 µm to about 5 µm MMAD, and most preferably in the range of about 2 µm to about 3 µm MMAD. The formulation of GLP-1 and GLP-1 analogs and derivatives is selected to yield the desired particle size in the chosen inhalation device.

Advantageously for administration as a dry powder, GLP-1 and GLP-1 analogs and derivatives are prepared in a particulate form resulting in an emitted particle size less than about 10 µm MMAD, preferably about 1 to about 5 µm MMAD, and most preferably about 2 µm to about 3 µm MMAD. The preferred particle size is effective for delivery to the alveoli of the patient's lung. Preferably, the dry powder is largely composed of particles-produced so that a majority of the particles have a size in the desired range. Advantageously, at least about 50% of the dry powder is made of particles having a diameter less than about 10 µm MMAD. Such formulations can be achieved by spray drying, milling, or critical point condensation of a solution containing the particular GLP-1 molecule and other desired ingredients. Other methods also suitable for generating particles useful in the current invention are known in the art.

The particles are usually separated from a dry powder formulation in a container and then transported into the lung of a patient via a carrier air stream. Typically, in current dry powder inhalers, the force for breaking up the solid is provided solely by the patient's inhalation. One suitable dry powder inhaler is the Turbohaler manufactured by Astra (S ödertalje, Sweden). In another type of inhaler, air flow generated by the patient's inhalation activates an impeller motor which deagglomerates the GLP-1 molecule particles. The Dura Spiros™ inhaler is such a device.

Formulations of GLP-1 and GLP-1 analogs and derivatives for administration from a dry powder inhaler typically include a finely divided dry powder containing peptide, but the powder can also include a bulking agent, carrier, excipient, another additive, or the like. Additives can be included in a dry powder formulation of GLP-1 and GLP-1 analogs and derivatives, for example, to dilute the powder as required for delivery from the particular powder inhaler, to facilitate processing of the formulation, to provide advantageous powder properties to the formulation, to facilitate dispersion of the powder from the inhalation device, to stabilize the formulation (e.g., antioxidants or buffers), to provide taste to the formulation, or the like. Advantageously, the additive does not adversely affect the patient's airways. The GLP-1 and GLP-1 analogs and derivatives can be mixed with an additive at a molecular level or the solid formulation can include particles of the peptide mixed with or coated on particles of the additive. Typical additives include mono-, di-, and polysaccharides; sugar alcohols and other polyols, such as, for example, lactose, glucose, raffinose, melezitose, lactitol, maltitol, trehalose, sucrose, mannitol, starch, or combinations thereof; surfactants, such as sorbitols, diphosphatidyl choline, or lecithin; or the like. Typically an additive, such as a bulking agent, is present in an amount effective for a purpose described above, often at about 50% to about 90% by weight of the formulation. Additional agents known in the art for formulating proteins can also be included in the formulation.

In another aspect of the invention a spray including GLP-1 and GLP-1 analogs and derivatives can be produced by forcing a suspension or solution of the peptide through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, proplets of GLP-1 and GLP-1 analogs and derivatives delivered by a sprayer have an inhaled droplet size less than about 10 µm MMAD, preferably in the range of about 1 µm to about 5 µm MMAD, and most preferably about 2 µm to about 3 µm MMAD.

Formulations of GLP-1 and GLP-1 analogs and derivatives suitable for use with a sprayer typically are about 1 mg to about 20 mg of the peptide per ml of solution. The formulation can include agents such as an excipient, a buffer, an isotonicity agent, a preservative, a surfactant, and metal cations. The formulation can also include an excipient or agent to stabilize the peptide such as a buffer, a reducing agent, a bulk protein, or a carbohydrate. Bulk proteins useful in formulating GLP-1 and GLP-1 analogs and derivatives include albumin, protamine, or the like. Typical carbohydrates useful in formulating GLP-1 and GLP-1 analogs and derivatives include sucrose, mannitol, lactose, trehalose, glucose, or the like. Formulations of GLP-1 and GLP-1 analogs and derivatives can also include a surfactant, which can reduce or prevent surface-induced aggregation of the peptide caused by atomization of the solution in forming an aerosol. Various conventional surfactants can be employed, such as polyoxyethylene fatty acid esters and alcohols, and polyoxyethylene sorbitol fatty acid esters. Amounts will generally range between 0.001 and 4% by weight of the formulation. Other surfactants such as diphosphatidyl choline or lecithin can also be used. Especially preferred surfactants for purposes of this invention are polyoxyethylene sorbitan monooleate, polysorbate 80, polysorbate 20, or the like. Additional agents known in the art for formulating proteins can also be included in the formulation.

GLP-1 and GLP-1 analogs and derivatives can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of the peptide through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the peptide formulation either directly or through a coupling fluid, creating an aerosol. Advantageously, droplets of GLP-1 and GLP-1 analogs and derivatives delivered by a nebulizer have a particle size less than about 10 µm MMAD, preferably in the range of about 1 µm to about 5 µm MMAD, and most preferably about 2 µm to about 3 µm MMAD.

Formulations of GLP-1 and GLP-1 analogs and derivatives suitable for use with a nebulizer, either jet or ultrasonic, typically include an aqueous solution of the peptide at a concentration of about 1 mg to about 20 mg per ml of solution. The formulation can include agents such as an excipient, a buffer, an isotonicity agent, a preservative, a surfactant, and a divalent metal cation. The formulation can also include an excipient or agent to stabilize the peptide, such as a buffer, a reducing agent, a bulk protein, or a carbohydrate. Bulk proteins useful in formulating GLP-1 and GLP-1 analogs and derivatives include albumin, protamine, or the like. Typical carbohydrates useful in formulating GLP-1 related proteins include sucrose, mannitol, lactose, trehalose, glucose, or the like. Formulations of the GLP-1 and GLP-1 analogs and derivatives can also include a surfactant, which can reduce or prevent surface-induced aggregation of the peptide caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Other surfactants such as phosphatidyl choline or lethicin can also be used. Especially preferred surfactants for purposes of this invention are polyoxyethylene sorbitan monooleate, polysorbate 80, polysorbate 20, or the like. Additional agents known in the art for formulation of a protein such as GLP-1 related molecules can also be included in the formulation.

Another aspect of the invention involves a metered dose inhaler (MDI). In this embodiment, a propellant, GLP-1 and GLP-1 analogs and derivatives, and any excipients or other additives are contained in a canister as a mixture including a liquefied compressed gas. Actuation of the metering valve releases the mixture as an aerosol, preferably containing inhaled particles in the size range of less than about 10 µm MMAD, preferably about 1 µm to about 5 µm MMAD, and most preferably about 2 µm to about 3 µm MMAD. The desired aerosol particle size can be obtained by employing a formulation of GLP-1 and GLP-1 analogs and derivatives produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of GLP-1 and GLP-1 analogs and derivatives for use with a metered-dose inhaler device will generally include a finely divided powder containing peptide as a suspension in a non aqueous medium, for example, suspended in a propellant with the aid of a surfactant. The propellant may be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluroalkane-227), or the like. Preferably the propellant is a hydrofluorocarbon. The surfactant can be chosen to stabilize the GLP-1 molecule as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Other surfactants such as diphosphatidyl choline or lethicin can also be used. Additional agents known in the art for formulating proteins can also be included in the formulation.

The present invention also relates to a pharmaceutical composition or formulation including GLP-1 and GLP-1 analogs and derivatives and suitable for administration by inhalation. According to the invention, GLP-1 and GLP-1 analogs and derivatives can be used for manufacturing a formulation or medicament suitable for administration by inhalation. The invention also relates to methods for manufacturing formulations including GLP-1 related molecules in a form that is suitable for administration by inhalation. For example, a dry powder formulation can be manufactured in several ways, using conventional techniques. Particles in the size range appropriate for maximal deposition in the lower respiratory tract can be made by micronizing, milling, spray drying, or the like. And a liquid formulation can be manufactured by dissolving the peptide in a suitable solvent, such as water, at an appropriate pH, including buffers or other excipients.

The present invention may be better understood with reference to the following examples. These examples are intended to be representative of specific embodiments of the invention, and are not intended as limiting the scope of the invention.

EXAMPLES

Serum Pharmacokinetics of Vale$^8$-GLP-1 in Beagle Dogs Following Pulmonary Administration The GLP-1 analog, Val$^8$-GLP-1(7-37)OH (SEQ ID NO:4) was prepared in *E coli* using conventional recombinant DNA techniques and purified to homogeneity.

NH$_2$,-His-Val-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly-OH (SEQ ID NO: 4)

One group of 6 female beagle dogs was exposed to inhaled Val$^8$-GLP-1 for 15 minutes at an average aerosol concentration of 77.2 µg/L generated from a solution of Va$^8$-GLP-1 in sterile water. These animals were dosed with 100 µg/kg via subcutaneous administration approximately 1-week after inhalation exposures. Tidal volume, breathing rate, and minute volume were monitored prior to and throughout the exposure period. Blood was collected for analysis of plasma levels of Val$^8$-GLP-1 at various time points following inhalation and subcutaneous administration. Bronchoalveolar lavage (BAL) fluid was collected approximately 4 hours postexposure and analyzed for LDH, total protein, cell counts, and white cell differentials.

The delivery of Val$^8$-GLP-1 was well tolerated with an inhaled dose of 1198 µg/kg and an estimated deposited lung dose of 240 µg/kg. Subcutaneous administration of 100 µg/kg was also well tolerated by all animals. Inhalation and subcutaneous administration of Val$^8$-GLP-1 was delivered using formulated and formulated material.

There were no treatment-related clinical observations; body weights were not adversely affected by Val$^8$-GLP-1. Only minor lung effects were observed. Increases in both tidal volume and minute volume were observed during the 15 minute inhalation exposures but the data were highly variable. No significant changes were observed for LDH, red blood cell counts, white blood cell counts, neutrophils, lymphocytes, eosinophils, epithelial cells, macrophages, basophils, or monocytes. There was a mild increase in total protein following aerosol delivery of Val$^8$-GLP-1.

Results from this study demonstrated that there was good bioavailability of Val$^8$-GLP-1(40%, based on AUC) delivered to the lungs of beagle dogs by inhalation relative to subcutaneous administration. Val$^8$-GLP-1 was well tolerated for up to 15 minutes with minimal effects on the lungs at an average inhaled dose of 1198 µg/kg, which was a no-observed-adverse-effects level (NOAFL) in this study.

Preparation of Dose Solutions

Solutions of Val$^8$-GLP-1 were prepared on the days of dosing at concentrations of 0.5 mg/ml or 8 mg/ml in sterile water for subcutaneous administration and pulmonary administration, respectively. An additional solution of Val$^8$-GLP-1(8 mg/ml) was prepared at the end of live phase in order to determine the particle size distribution of aerosolized Val$^8$-GLP-1. The solutions were filtered through a low protein binding 0.22 micron canister filter. The pH of the solution was adjusted with sodium hydroxide solution to 7.47.

Test Animals

Six females Beagle dogs (Marshall Farms, North Rose, N.Y.) were used in this study. Each animal was uniquely identified by a five-digit animal number and a seven-digit tattoo (located on inner ear) number recorded on their cage card. All of the animals were acclimated to the restraint slings prior to beginning the study. The weight range of the animals at the start of the study was 8.4 to 11.1 kg. The age of the animals at the start of the study was 33 to 37 weeks.

Test Animal Housing and Care

Animals were pair housed in stainless steel cages except on the days of exposure. Each animal was individually housed on the day of exposure in order to monitor their feeding regimen. Rooms were thermostatically set to maintain a temperature of 70° F. and maintain the actual temperature within ±8° F. from that set point. The environmental control system is designed to maintain a relative humidity of 20% and a maximum of 80%. Light was on a 12-hour cycle, with lights on between 0600 and 1800 hours. Subsequently, lights were off between 1800 and 0600 hours except when blood samples were collected. Animals were fed once daily with Hill's Science Diet. Animals were fasted for approximately 12-hours prior to exposure. Tap water was provided ad libitum except during exposures.

Treatment Groups and Study Duration

All 6 dogs were exposed for 15 minutes to aerosolized Val$^8$-GLP-1. The targeted deposited lung dose for Val$^8$-GLP-1 exposures was 200 µg/kg of body weight. Approximately 7 days after pulmonary administration of Val$^8$-GLP-1, all dogs were dosed with 100 µg/kg Val$^8$-GLP-1 of body weight via subcutaneous administration.

Exposure System

The dogs were tested while standing in restraint slings. Two layers of 0.03 inch latex sheets were placed around the animals' necks to form a nonrestrictive airtight seal. A custom built, 11-L head-dome, similar to that described by Allen et al. (J Appl Toxicol 1995; 15:13–17) was placed over the dogs' heads and secured to the sling. Airflow was exhaust driven via a transvector located on the exhaust side of the dome. Because the helmet was airtight and the neck was sealed, this constituted a head-only exposure system. The total flow rate through the dome was approximately 7.5 L/min.

Aerosol Generation

The aerosols were generated using a Respirgard II nebulizer with an input of approximately 6.5 L/min. The output from the generator flowed directly into the head-dome.

Atmospheric Concentration Sampling

All sampling for total gravimetric concentrations was performed with in-line filter holders containing type AlB glass fiber filters (Gelman Instruments Co., Ann Arbor, Mich.). Filters sampling from the chamber was carried out at a nominal sampling rate of 1 L/min, calibrated with a portable mass airflow calibrator (Model 830, Sierra Instruments, Carmel Valley, Calif.). Sampling duration was 15 minutes. Particle size analysis was performed with a Sierra Model 218K Ambient Cascade Impactor (Anderson Samplers, Inc, Atlanta, Ga.). Cascade sampling from the chamber was carried out at a nominal sampling rate of 3 L/min, calibrated with a portable mass airflow calibrator (Model 830, Sierra Instruments, Carmel Valley, Calif.). Sampling duration was 31 minutes. Filters were allowed to dry for approximately 30-minutes before being re-weighed.

Dose Determination

The dose of $Val^8$-GLP-1 inhaled during a 15-minute exposure was estimated as follows: the mean minute volume (mL) during the 15 minute exposure was multiplied by the exposure duration to yield the total air breathed (L) during the inhalation exposure. This value was multiplied by the aerosol concentration (μg/L) to determine total dose (mg). The inhaled dose (μg/kg) was calculated by dividing the total dose (μg) by the animal's body weight (kg).

The dose of $Val^8$-GLP-1 deposited in the lungs was estimated as follows: inhaled dose (μg/kg) was multiplied by 20 percent to yield estimated deposited lung dose (μg/kg). Aerosols with a MMEAD ranging from 1–2 μm MMAD have been shown to deposit in the lung with approximately a 20 percent efficiency (Schlesinger RB. 1985. Comparative deposition of inhaled aerosols in experimentalanimals and humans: a review. J Toxicol Environ Health 15:197–214).

Pulmonary Function

All animals were weighed on Days −5, 0, and 7. Breathing patterns (tidal volume, breathing frequency, and minute volume) were monitored using a size '0' pneumotachograph connected to a port on the head-dome. The signals were collected on a personal computer using the Buxco XA Data Acquisition System (Buxco Electronics, Inc, Sharon, Conn.). At least 15 minutes of preexposure data were collected before the exposures began, followed by data collection throughout the 15-minute exposure periods. All data were analyzed as 5-minute averages.

Bronchoalveolar Lavage

Bronchoalveolar lavage (BAL) was performed approximately 4 hours after each dosing regimen. The animals were anesthetized with an intravenous injection of 2% Brevital prior to the BAL procedure. Bronchoalveolar lavage was performed using a pediatric fiberoptic bronchoscope (Olympus, model BF, Type 3C10, Lake Success, N.Y.). The bronchoscope tip was wedged in a $5^{th\ to\ 7th}$ generation airway of a lower lobe. The BALs were alternated between the right and left lung lobes. Two 10-mL aliquots were instilled and gently suctioned out. Aliquots of the recovered lavage fluid were used to determine total white cell counts, total red cell counts, white cell differentials, total protein, and lactate dehydrogenase.

Cell Counts and Differentials

A complete blood count was done on the unconcentrated BAL fluid using a Technicon H1 System (Technicon Instruments Corporation). Cell differentials for the BAL were done by microscopic evaluation of 200 Wright stained cells.

Blood Collection

For analysis of plasma pharmacokinetics of $Val^8$GLP-1, approximately 2 to 3 mL of blood were collected in EDTA vacutainer tubes from the cephalic or jugular vein prior to exposure and at 0.25, 0.5, 1, 2, 3, 4, 6, 8, and 12 hours postexposure. To obtain the plasma, each tube was centrifuged at approximately 3000 rpm for 10 minutes at 10° C. The plasma samples were stored at −70° C. until sent for assay.

Exposure Concentration/Particle Size and Lung Dose

The average exposure concentration for each dog exposed to $Val^8$-GLP-1 ranged from 64.0 to 101.3 μg/L. The mean (±SD) concentration for all animals was 77.2±16.9 μg/L. Particle size was measured as a mass median equivilant aerodynamic diameter (MMEAD) of 0.91 μm with a geometric standard deviation (GSD) of 2.37.

The average dose of $Val^8$a-GLP-1 deposited in lungs of 6 dogs treated with $Val^8$-GLP-1 was calculated as 240±42 μg/kg (means±SD). The mean inhaled dose (that which entered the respiratory tract neglecting deposition) was 1198±208 μg/kg (mean±SD). Individual animal data are shown in the table below.

Estimated Lung Dose for Animals Exposed to Aerosols of $Val^a$-GLP-1

| Animal Number | Aerosol Conc. (μg/L) | Average Minute Volume (ml) | Inhaled Lung Dose (μg/kg) | Deposited Lung Dose (μg/kg) |
|---|---|---|---|---|
| 27682 | 0.07717* | 8406 | 1060 | 212 |
| 27684 | 0.07717* | 9563 | 1030 | 206 |
| 27685 | 0.10133 | 7260 | 1350 | 270 |
| 27686 | 0.06400 | 12733 | 1360 | 272 |
| 27687 | 0.06733 | 9214 | 950 | 190 |
| 27689 | 0.07600 | 11890 | 1400 | 288 |

*Aerosol concentration was not determined for animals 27682 and 27684, therefore the mean aerosol concentration was used to calculate an estimated inhaled lung dose (μg/kg).

No significant changes in body weight were observed during the treatment phase. The initial (Day −5) and final (Day 7) body weights were 9.5±0.9 (mean±SD; n=6) and 9.7±0.9 kg, respectively. No marked changes in breathing frequency was observed. Slight increases in tidal volume and minute volume were measured but the data was highly variable potentially due to the short acclimation period prior to study initiation. Individual animal data are shown in the table below.

| | Changes in Pulmonary Function During Exposure to Val$^a$-GLP-1 | | | | | | | | |
|---|---|---|---|---|---|---|---|---|---|
| Animal | Tidal Volume (mL) | | | Breathing Frequency (bpm) | | | Minute Volume (mL/min) | | |
| Number | 5* | 10* | 15% | 5* | 10* | 15* | 5* | 10* | 15* |
| 27682 | 119.0 | 152.1 | 105.1 | 74 | 86.0 | 95.7 | 7265 | 9360 | 8592 |
| 27684 | 104.6 | 99.4 | 100.8 | 119.2 | 118.2 | 108.7 | 10300 | 9117 | 9272 |
| 27685 | 165.9 | 178.5 | 209.6 | 58.1 | 49.4 | 42.5 | 7938 | 7465 | 6377 |
| 27686 | 325.1 | 586.2 | 374.4 | 56.3 | 33.8 | 59.4 | 12200 | 13300 | 12700 |
| 27687 | 245.9 | 221.6 | 183.1 | 39.5 | 45.5 | 50.5 | 9288 | 9573 | 8781 |
| 27689 | 184.5 | 367.6 | 454.0 | 39.8 | 46.8 | 33.3 | 7271 | 13400 | 15000 |
| Mean | 190.8 | 267.6 | 237.8 | 64.6 | 63.3 | 65.0 | 9044 | 10369 | 10120 |
| Stdev | 82.8 | 180.7 | 145.3 | 29.8 | 32.2 | 30.3 | 1956 | 2426.1 | 3141 |
| Mean (baseline) | 239.0 | 216.8 | 207.6** | 45.9 | 51.4 | 64.4** | 8448 | 8744.8 | 8223** |
| Stdev (baseline) | 161.4 | 137.2 | 209.5 | 12 | 10.2 | 32.3 | 2614 | 2614 | 1566 |

*minutes during exposure (values represent average over 5 minutes)
**mean calculated from a n = 5 (instead of n = 6) because no value was recorded for animal #27689 at 15 minutes preexposure

| | Comparison of Pharmacokinetics Following Subcutaneous and Pulmonary Administration of Val$^a$-GLP-1 | | | |
|---|---|---|---|---|
| Delivery Route | $C_{max}$ (ng/mL) | $T_{max}$ (h) | $AUC_{0-t(1)}$ (ng * h/mL) | $T\frac{1}{2}(\alpha)$ (hours) |
| Subcutaneous | 10.53 ± 1.06 | 0.71 ± 0.14 | 36.37 ± 2.18 | 1.26 ± 0.11 |
| Inhalation | 8.66 ± 0.90 | 1.54 ± 0.59 | 35.21 ± 5.91 | 1.19 ± 0.11 |

*All values are reported as mean ± SEM (standard error of the mean).
$_{(1)}AUC_{0-t}$ = area under the plasma concentration curve from time 0 to t, where t ≈ 12 hours postdose Plasma concentrations of immunoreactive Val$^8$-GLP-1 (Table 3) were measured by a competitive radioimmunoassay (RIA). The absorption of Val$^8$-GLP-1 via both delivery routes appeared to be rapid, reaching substantial plasma concentrations at 15 minutes postdose. The plasma time profiles were similar for the subcutaneous injections and inhalation. The average Tmax value for inhalation was greater than that for subcutaneous injection. Also, the elevated plasma Val$^8$t-GLP-1 concentration (close to Cmax) achieved by inhalation appeared to remain near that level for a longer period of time than following subcutaneous injection.

Based on the average AUC values, the bioavailability of inhaled Val$^8$-GLP-1 (averaged inhaled dose of 1198 μg/kg) relative to subcutaneous injection (100 μg/kg) was approximately 7.7%. On the basis of deposited lung dose, estimated as 240 μg/kg, the bioavailability relative to subcutaneous injection was 40%.

We claim:

1. A method of administering a glucagon-like peptide-1 (GLP-1) molecule by inhalation to the lungs of a patient for a time and under conditions effective to lower plasma glucose, wherein the GLP-1 molecule has an amino acid sequence of a formula:

$R_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$ (SEQ ID NO: 1)

wherein:

$R_1$ is selected from the group consisting of L-histidine, D-histidine, desamino-histidine, 2-amino-histidine, beta-hydroxy-histidine, homohistidine, alpha-fluoromethyl-histidine, and alpha-methylhistidine;

X is selected from the group consisting of Gly, Val, Thr, Ile, and alpha-methyl-Ala;

Y is selected from the group consisting of Glu, Gln, Ala, Thr, Ser, and Gly;

Z is selected from the group consisting of Glu, Gln, Ala, Thr, Ser, and Gly; and $R_2$ is selected from the group consisting of $NH_2$, and Gly-OH.

2. The method of claim 1, wherein the GLP-1 molecule is selected from the group consisting of $Gly^8$-GLP-1(7-36)

$NH_2$, $Val^8$-GLP-1(7-37)OH, alpha-methyl-$Ala^8$-GLP-1(7-36)$NH_2$, and $Gly^8$-$Gln^{21}$-GLP-1(7-37)OH.

3. The method of claim 1, wherein the GLP-1 molecule is $Val^8$-GLP-1(7-37)OH or $Gly^8$-GLP-1(7-37)OH.

4. The method of claim 3, wherein the GLP-1 molecule is $Val^8$-GLP-1(7-37)OH.

5. The method of claim 1, wherein the GLP-1 molecule is in the form of a dry powder.

6. The method of claim 5, wherein the dry powder has a particle size of about 10 microns mass median aerodynamic diameter.

7. The method of claim 6, wherein the dry powder has a particle size of less than 10 microns mass median aerodynamic diameter.

8. The method of claim 7, wherein the dry powder has a particle size of about 1 to about 5 microns mass median aerodynamic diameter.

9. The method of claim 8, wherein the dry powder has a particle size of about 2 to about 3 microns mass median aerodynamic diameter.

10. The method of claim 5, wherein the GLP-1 molecule is delivered from an inhalation device selected from the group consisting of a nebulizer, a metered-dose inhaler, a dry powder inhaler, and a sprayer.

11. The method of claim 10, wherein the device is a sprayer or a dry powder inhaler.

12. The method of claim 11, wherein an actuation of the device administers about 40 µg to about 4,000 µg of the GLP-1 molecule.

13. The method of claim 12, wherein an actuation of the device administers about 80 µg to about 2,000 µg of the GLP-1 molecule.

14. The method of claim 13, wherein an actuation of the device administers about 160 µg to about 1,000 µg of the GLP-1 molecule.

15. The method of claim 14, wherein an actuation of the device administers about 320 µg to about 500 µg of the GLP-1 molecule.

16. The method of claim 1, wherein the GLP-1 molecule is administered as an aerosol.

17. The method of claim 16, wherein the GLP-1 molecule is delivered from an inhalation device selected from the group consisting of a nebulizer, a metered-dose inhaler, and a sprayer.

18. A method of administering a GLP-1 molecule by inhalation to the lungs of a patient for a time and under conditions effective to lower plasma glucose, wherein the GLP-1 molecule comprises an amino acid sequence of a formula:

$R_1$-X-Glu-Gly-Thr-Phe-Thr-Ser-Asp-Val-Ser-Ser-Tyr-Leu-Y-Gly-Gln-Ala-Ala-Lys-Z-Phe-Ile-Ala-Trp-Leu-Val-Lys-Gly-Arg-$R_2$ (SEQ ID NO:1)

wherein:

$R_1$ is selected from the group consisting of L-histidine, D-histidine, desamino-histidine, 2-amino-histidine, beta-hydroxy-histidine, homohistidine, alpha-fluoromethyl-histidine, and alpha-methyl-histidine;

X is selected from the proup consisting of Gly, Val, Thr, Ile, and alpha-methyl-Ala;

Y is selected from the group consisting of Glu, Gln, Ala, Thr, Ser, and Gly;

Z is selected from the group consisting of Glu, Gln, Ala, Thr, Ser, and Gly; and $R_2$ is selected from the group consisting of $NH^2$, and Gly-OH and wherein the GLP-1 molecule further comprises one additional substitution compared with GLP-1.

19. The method of claim 18, wherein X is valine.

20. The method of claim 18, wherein X is glycine.

21. The method of claim 19, wherein the GLP-1 molecule is in the form of a dry powder.

22. The method of claim 21, wherein the GLP-1 molecule is delivered from an inhalation device selected from the group consisting of a nebulizer, a metered-dose inhaler, a dry powder inhaler, and a sprayer.

23. The method of claim 19, wherein the GLP-1 molecule is administered as an aerosol.

24. The method of claim 23, wherein the GLP-1 molecule is delivered from an inhalation device is selected from the group consisting of a nebulizer, a metered-dose inhaler, and a sprayer.

25. The method of claim 20 wherein the GLP-1 molecule is in the form of a dry powder.

26. The method of claim 25 wherein the GLP-1 molecule is delivered from an inhalation device selected from the group consisting of a nebulizer, a metered-dose inhaler, a dry powder inhaler, and a sprayer.

27. The method of claim 20, wherein the GLP-1 molecule is administered as an aerosol.

28. The method of claim 27, wherein the GLP-1 molecule is delivered from an inhalation device is selected from the group consisting of a nebulizer, a metered-dose inhaler, and a sprayer.

* * * * *